(12) United States Patent
Brouqueyre et al.

(10) Patent No.: US 9,901,198 B2
(45) Date of Patent: Feb. 27, 2018

(54) PILLOW SYSTEM PROVIDING SOUND SUPPRESSION

(71) Applicant: KONINKLIJKE PHILIPS N.V., Eindhoven (NL)

(72) Inventors: Laurent Brouqueyre, Kennesaw, GA (US); Mark Wayne Barclay, Saxonburg, PA (US); Peter Douglas Hill, Monroeville, PA (US); Lauren Elizabeth Hueser, Brighton, MA (US); Reenu John, Monroeville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 91 days.

(21) Appl. No.: 14/425,204

(22) PCT Filed: Aug. 29, 2013

(86) PCT No.: PCT/IB2013/058124
§ 371 (c)(1),
(2) Date: Mar. 2, 2015

(87) PCT Pub. No.: WO2014/037855
PCT Pub. Date: Mar. 13, 2014

(65) Prior Publication Data
US 2015/0216334 A1    Aug. 6, 2015

Related U.S. Application Data

(60) Provisional application No. 61/696,460, filed on Sep. 4, 2012.

(51) Int. Cl.
*A47G 9/10* (2006.01)
*A61F 5/56* (2006.01)
(Continued)

(52) U.S. Cl.
CPC ......... *A47G 9/1009* (2013.01); *A47G 9/1045* (2013.01); *A61F 5/56* (2013.01);
(Continued)

(58) Field of Classification Search
CPC ...... A47G 9/10; A47G 9/1009; A47G 9/1045; A47G 9/1081; A47G 2009/006;
(Continued)

(56) References Cited

U.S. PATENT DOCUMENTS 1,940,904 A * 12/1933 Dayton ................ A61F 5/03
602/19
4,447,922 A * 5/1984 Brochu ................ A47D 1/103
297/391
(Continued)

FOREIGN PATENT DOCUMENTS

CN        2047524 U     11/1989
CN        2201000 Y     6/1995
(Continued)

*Primary Examiner* — Nicholas F Polito
*Assistant Examiner* — David R Hare (57) ABSTRACT

The present disclosure pertains to a pillow system (40), in particular a pillow system that surrounds the subject's head. In some embodiments, the pillow system provides sound suppression. In some embodiments used with positive airways pressure ("PAP") systems, the pillow system includes a tube that delivers breathable gas to a mask.

17 Claims, 9 Drawing Sheets

(51) Int. Cl.
*A61M 16/06* (2006.01)
*G04B 47/02* (2006.01)
*G10K 15/04* (2006.01)
*G10K 11/178* (2006.01)
*A47G 9/00* (2006.01)

(52) U.S. Cl.
CPC ......... *A61M 16/0683* (2013.01); *G04B 47/02* (2013.01); *G10K 15/04* (2013.01); *A47G 2009/006* (2013.01); *A61M 2209/082* (2013.01); *G10K 11/178* (2013.01); *G10K 2210/116* (2013.01); *G10K 2210/3221* (2013.01)

(58) Field of Classification Search
CPC .. G04B 47/02; G10K 15/04; G10K 2210/116; G10K 2210/3221; G10K 11/178; A61M 16/0683; A61M 2209/082; A61F 5/56
See application file for complete search history.

(56) References Cited

U.S. PATENT DOCUMENTS

| | | | | | |
|---|---|---|---|---|---|
| 4,550,458 | A | * | 11/1985 | Fiore | A47C 7/383 297/393 |
| 4,616,639 | A | * | 10/1986 | Huber | A61F 5/01 128/99.1 |
| 4,679,263 | A | * | 7/1987 | Honer | A47C 7/383 297/393 |
| 5,072,429 | A | * | 12/1991 | Mair | A47G 9/1045 368/10 |
| 5,313,678 | A | * | 5/1994 | Redewill | A47C 21/003 297/393 |
| 5,813,065 | A | * | 9/1998 | Tinhorn | A47G 9/10 5/636 |
| 5,974,607 | A | * | 11/1999 | Smith | A61G 7/072 297/393 |
| 6,098,220 | A | * | 8/2000 | Momma | A47G 9/1009 5/636 |
| 6,481,031 | B1 | | 11/2002 | Hwang | |
| 6,651,256 | B1 | * | 11/2003 | Swift | A42B 1/004 2/15 |
| 6,658,681 | B2 | * | 12/2003 | Britto | A47D 13/083 5/636 |
| D576,439 | S | * | 9/2008 | Yaroshenko | D6/601 |
| 7,428,763 | B2 | * | 9/2008 | Hightower | A47G 9/10 5/636 |
| 7,451,507 | B2 | * | 11/2008 | Brinkerhoff | A61G 13/12 5/637 |
| 7,926,133 | B2 | * | 4/2011 | Xiao | A47G 9/1045 5/636 |
| 8,566,986 | B1 | * | 10/2013 | Chu | A47G 9/1045 5/636 |
| 9,032,570 | B1 | * | 5/2015 | Benami | A47G 9/1045 5/640 |
| 2003/0135927 | A1 | * | 7/2003 | Hsia | A47G 9/1009 5/640 |
| 2008/0216244 | A1 | * | 9/2008 | Minton | A47G 9/10 5/640 |
| 2009/0019641 | A1 | * | 1/2009 | Ali | B60N 2/4882 5/636 |
| 2011/0295083 | A1 | * | 12/2011 | Doelling | A61B 5/103 600/301 |
| 2014/0317849 | A1 | * | 10/2014 | Legrand | A47G 9/1045 5/636 |
| 2015/0216337 | A1 | * | 8/2015 | Brouqueyre | A47G 9/1009 128/866 |

FOREIGN PATENT DOCUMENTS

| | | |
|---|---|---|
| CN | 2440411 Y | 8/2001 |
| CN | 201959059 U | 9/2011 |
| GB | 2462514 A | 2/2010 |
| JP | 11253286 A | 9/1999 |
| JP | 2011030634 A | 2/2011 |
| KR | 20120015609 A1 | 2/2012 |
| WO | 2009073671 A1 | 6/2009 |
| WO | 2011082349 A1 | 7/2011 |

* cited by examiner

PILLOW SYSTEM PROVIDING SOUND SUPPRESSION

CROSS-REFERENCE TO PRIOR APPLICATIONS

This application is the U.S. National Phase application under 35 U.S.C. § 371 of International Application No. PCT/IB2013/058124, filed on Aug. 29, 2013, which claims the benefit of U.S. Provisional Patent Application No. 61/696,460, filed on Sep. 4, 2012. These applications are hereby incorporated by reference herein.

The present disclosure pertains to a pillow system that moves with the subject.

Many people do not get the necessary sleep because they are light sleepers, have trouble entering restful sleep, or have other disorders such as sleep apnea. Many subjects with sleep apnea wear a mask and use a positive airway pressure system to treat their apnea to alleviate the symptoms.

With normal pillows, the mask worn by subjects with sleep apnea can either shift out of place during the night or press uncomfortably on the subject's face. Some pillows have been developed for subjects with sleep apnea with the goal of overcoming the problems that mask-wearing subjects encounter with normal pillows. These pillows have contours that accommodate the shape of the mask so that the subject can rest their head on the pillow without discomfort from the mask. If the person moves their head while sleeping, the mask may still shift out of place or the tubing may become tangled.

Some subjects with masks use a tube management system when they sleep. Tube management systems are typically a hook-like arm positioned beside the bed that extends over the bed and suspends the mask's tubing above the subject.

Accordingly, it is an aspect of one or more embodiments of the present disclosure to provide a pillow system configured to engage the back and sides of a subject's head. In some instances, cushioning material is configured to engage the back and sides of a subject's head responsive to the head of the subject being in place on the pillow system. There is also a resilient frame configured to surround the back and sides of the subject's head to hold the cushioning material in place on the subject's head. The frame includes a first portion having a first inner side and a first outer side, with the first portion being configured to hold the cushioning material in place on a first side of the subject's head responsive to the subject's head being in place on the pillow system. There is also a second portion having a second inner side and a second outer side, with the second portion being configured to hold the cushioning material in place on a second side of the subject's head responsive to the subject's head being in place on the pillow system. To join the portions, there is an adjustable portion at a location proximate to the back of the subject's head that connects the first portion and the second portion, with the adjustable portion providing adjustment to accommodate differences in distances between the first side of the head and the second side of the head for different subjects. There are also, in some embodiments, ear cups. There is a first ear cup supported by the first portion and/or the cushioning material adjacent the first portion at a position such that, responsive to the subject's head being in place on the pillow, the first ear cup surrounds the subject's ear on a first side of the subject's head. There is also a second ear cup supported by the second portion and/or the cushioning material adjacent the second portion at a position such that, responsive to the subject's head being in place on the pillow, the second ear cup surrounds the subject's ear on a second side of the subject's head.

Several variations of the disclosure are contemplated. In some embodiments, the adjustable portion of the pillow includes one or more springs that slidably connect the first portion and second portion and biases the first portion toward the second portion. There may also be, in some embodiments, an alarm clock that can make noise and/or vibrate. In some instances, the first and second ear cups each include or are made of a noise-cancelling gel or foam. Alternatively, each ear cup may include a speaker and each speaker provides active noise cancellation.

In some embodiments, the pillow system also has a microphone. The microphone can be used for sound input generally, and can also be used when paired with one or more processors that execute a snoring detection module. The snoring detection module detects whether or not the subject is snoring based on signals generated by the microphone. In some instances, the pillow also has an alarm clock. In these embodiments, the processors also execute an output module that activates the alarm clock if the snoring detection module determines that the subject is snoring. When activated, the alarm clock may make noise and/or vibrate. In some embodiments, the alarm clock, snoring detection module, processors, and/or microphone are incorporated into one housing.

It is yet another aspect of one or more embodiments of the present disclosure to provide a method, which is used in a pillow system in one embodiment that includes a cushioning material, a resilient frame, a first ear cup and a second ear cup. The method involves engaging, by the cushioning material, the back and sides of a subject's head responsive to the head of the subject being in place on the pillow system. The method also involves surrounding, by the resilient frame, the back and sides of the subject's head and holding the cushioning material in place on the subject's head responsive to the subject's head being in place on the pillow system. Further, the first ear cup surrounds the subject's ear on a first side of the subject's head responsive to the subject's head being in place on the pillow and the second ear cup surrounds the subject's ear on a second side of the subject's head responsive to the subject's head being in place on the pillow system.

In some embodiments, the method also includes adjusting the frame to accommodate differences in distances between the first side of the head and the second side of the head for different subjects. The method may also include providing active noise cancellation via speakers housed in each of the first and second ear cups. Or, instead, the provided speaker may output sound, e.g., music, and each speaker is in signal communication with a sound producing device such as a radio or audio/music device, e.g., an MP3 player. In some instances, the method also includes detecting that the subject is snoring and in response, activating an alarm clock. The alarm clock may also activate in response to the user setting the alarm clock to activate at a certain time. The alarm clock can make noise and/or vibrate.

It is yet another aspect of one or more embodiments to provide a means for providing a pillow comprising: cushioning means for engaging the back and sides of a subject's head responsive to the head of the subject being in place on the pillow system; resilient means for surrounding the back and sides of the subject's head and holding the engaging means in place on the subject's head responsive to the head of the subject being in place on the pillow system; a first cup means for surrounding the subject's ear on a first side of the subject's head responsive to the subject's head being in place on the pillow system; and a second cup means for surrounding the subject's ear on a second side of the subject's head responsive to the subject's head being in place on the pillow system.

In some instances, the pillow includes means for adjusting the resilient means to accommodate differences in distances between the first side of the head and the second side of the head for different subjects. The pillow, in some embodiments, also includes active noise cancellation means housed in each of the first and second cup means. Additionally or alternatively, there may also be sound output means housed in each of the first and second cup means. As above, in some embodiments, there is also detecting means for detecting that the subject is snoring, which, in response to detecting that the user is snoring, there are means for activating an alarm.

These and other aspects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
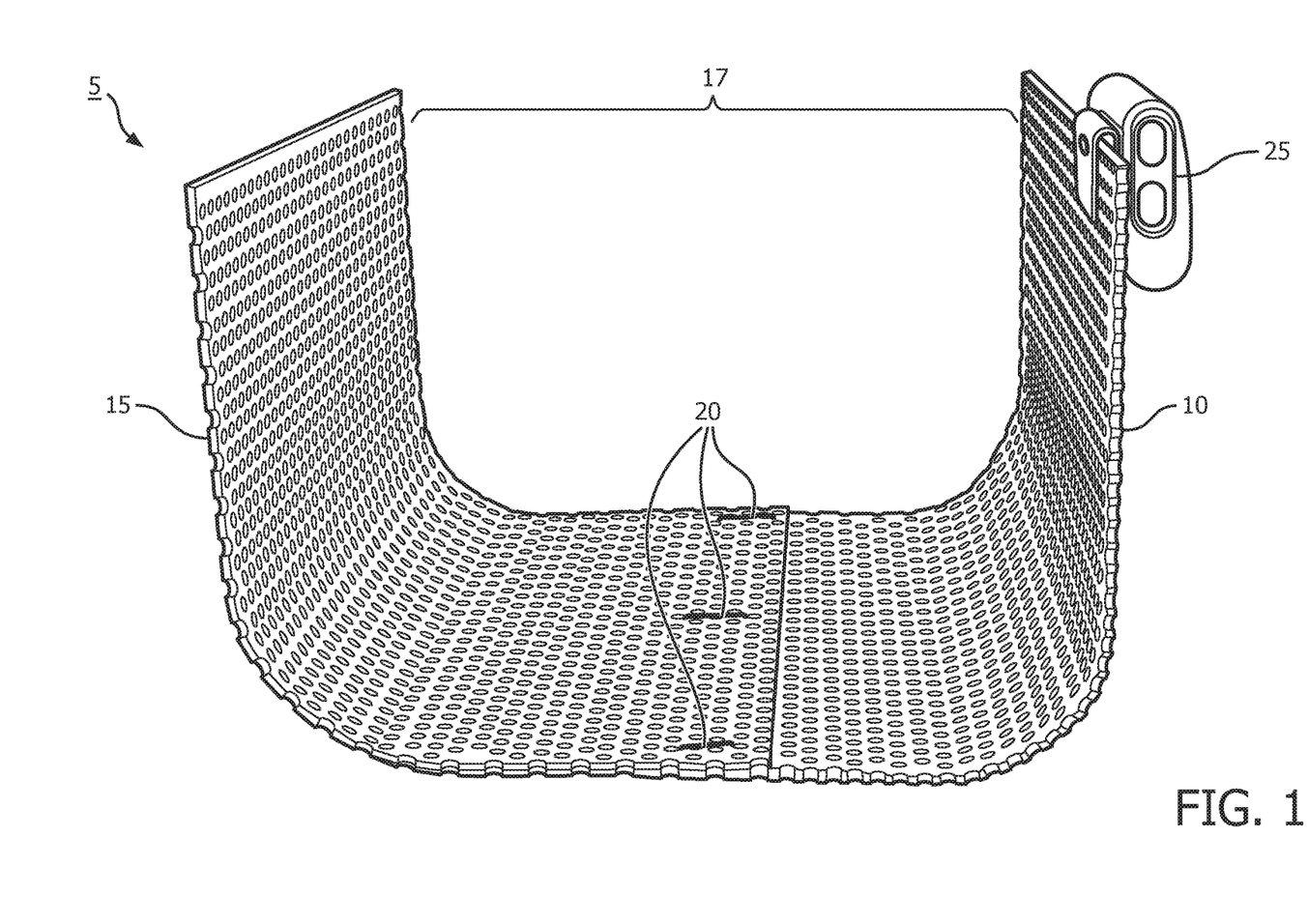
FIG. 1 illustrates an exemplary embodiment of a frame used in a pillow system.

FIG. 1 illustrates an exemplary embodiment of a frame 5 used in a pillow system 40. In one embodiment, frame 5 is composed of two portions, a portion 10 for the back and left of the subject's head and a portion 15 for the back and right of the subject's head. Portions 10, 15 of frame 5, in some embodiments, are made from Polyvinyl Chloride (PVC) material. In some embodiments, portion 10, 15 of frame 5 can be made from other plastic materials, e.g., Polyethylene terephthalate (PET), Nylon, or fiber glass, carbon fiber and epoxy. In some embodiments, e.g., depicted in FIG. 1, portions 10, 15 are perforated and have holes throughout. This reduces the weight of frame 5.

In one embodiment, the materials that make up portions 10, 15 of frame 5 are substantially resilient and rigid. In this embodiment, the vertical parts of portions 10, 15 do not substantially flex if force is applied, e.g., when a subject's head is placed into pillow system 40, the sides of the subject's head push against portions 10, 15. When force is applied, the vertical parts of portions 10, 15 maintain their vertical orientation and the U-shape of frame 5 is maintained because instead of flexing, vertical parts of portions 10, 15 exert a force against adjusting portion 20, causing the bottom of the U-shape of the frame to widen.

In another embodiment, portions 10, 15 are generally resilient, but have some flexibility. In this embodiment, the vertical parts of portions 10, 15 flex slightly if force is applied so as not to be uncomfortable for the subject when his head is inserted into the pillow system 40. However, the U-shape of frame 5 is generally maintained because vertical parts of portions 10, 15 are generally resilient and exert a force against adjusting portion 20, causing the bottom of the U-shape of the frame to widen.

Figure 4:
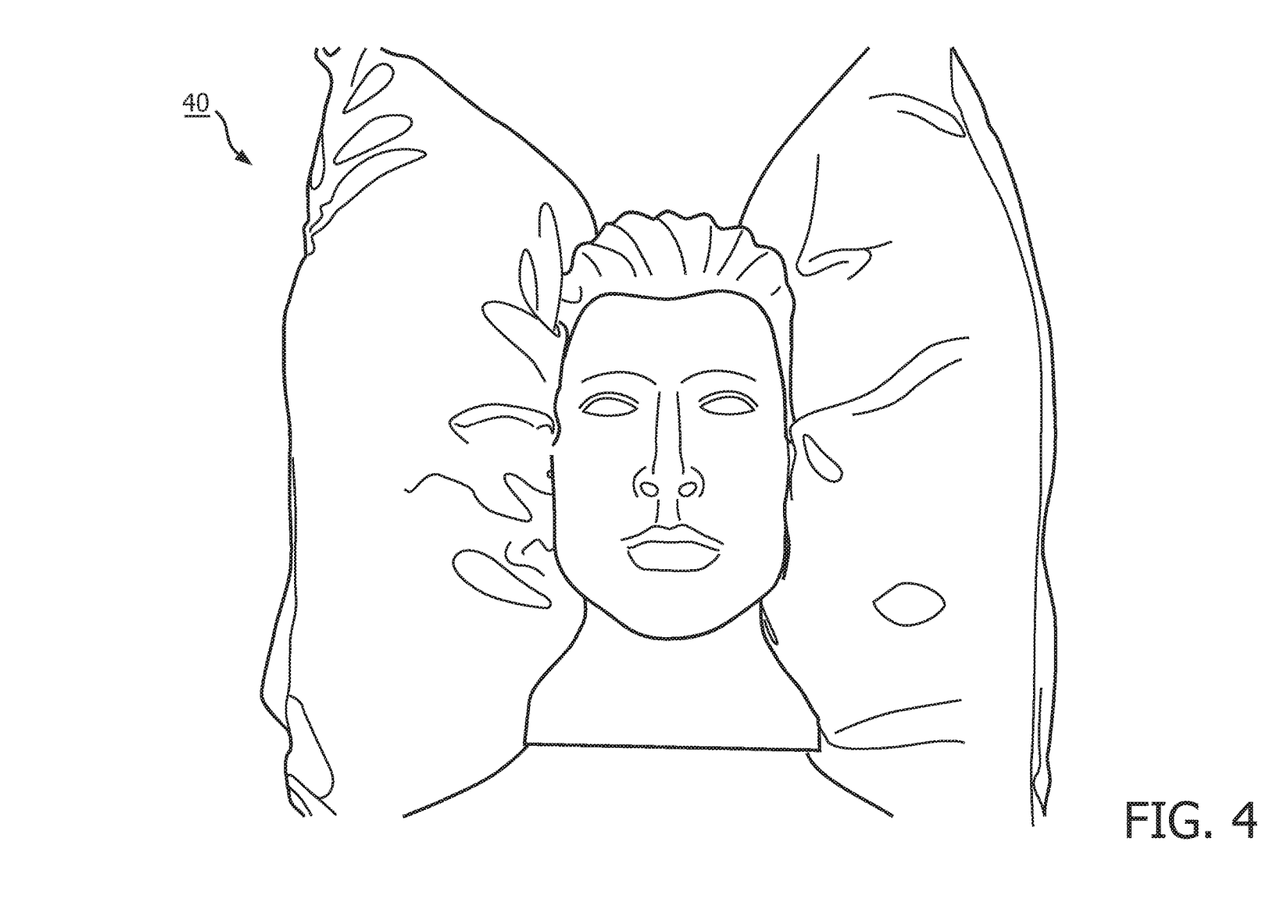
FIG. 4 depicts an exemplary view of a subject's head in place on pillow system.

In some embodiments, the portions 10, 15 are somewhat resilient, but are generally flexible. In this embodiment, the vertical parts of portions 10, 15 flex significantly if force is applied so as not to be uncomfortable for the subject when his head is inserted into the pillow system 40 (as shown in FIG. 4). The U-shape of frame 5 is somewhat maintained because vertical parts of portions 10, 15 are somewhat resilient and exert a force against adjusting portion 20, causing the bottom of the U-shape of the frame to slightly widen.

In some embodiments, when the force is removed, e.g., the subject's head is removed from the pillow system 40, portions 10, 15 stop exerting force against adjusting portion 20 and are biased back together. In some embodiments, to the extent the vertical parts of portions 10, 15 flexed, the vertical parts of portions 10, 15 return to their vertical position. In some embodiments though, once adjusting portion 20 is adjusted, it maintains its adjustment and portions 10, 15 are not biased back together.

With respect to the subject's head, typically the frame extends from approximately the top of the subject's head to just below the chin. An embodiment of a pillow system incorporating frame 5 is depicted in FIG. 4.

As shown in FIG. 1, there is an opening 17 between portions 10, 15, for the subject to insert his head. Portions 10, 15 are connected by an adjustable portion 20. In some embodiments, connector 20 slidably connects portions 10, 15 at a position that corresponds to the back 39 of the user's head. In some cases, adjustable portion 20 is a series, e.g., a set of three, of springs. When the subject's head is placed into a pillow system that incorporates frame 5, portions 10, 15 are pushed apart by the sides of the subject's head. In one embodiment, adjustable portion 20 biases portion 10 and portion 15 together in response, thereby creating a snug fit between the subject's head and the pillow system. Alternatively or additionally, adjustable portion 20 can optionally include a ball catch system. In embodiments described above where portion 10, 15 are perforated, the catch of the ball catch system can be the perforation holes. Other mechanisms for connecting and/or adjusting frame 5 are contemplated. In another embodiment, adjustable portion 20 is an integral and bendable material that maintains its shape once it is adjusted. As a result, portions 10, 15 remain at a generally fixed distance apart until adjustable portion 20 is adjusted again. In those embodiments, adjustable portion may be made of a malleable metal or plastic.

In some embodiments, an alarm clock 25 may be attached to frame 5, e.g., via a clip (as shown in FIG. 1), bolts or screws. Although alarm clock 25 is depicted as attached to portion 10, it can be attached to portion 15 or elsewhere on frame 5 or within the pillow system cushioning material. Alarm clock 25 can make noise and/or vibrate. In some embodiments, the alarm clock 25 housing includes a processor which executes a snoring detection module, and/or includes a microphone. In other embodiments, the alarm clock may be in wired or wireless communication with a snoring detection module that is executing on a processor located outside the alarm clock 25 but still in the pillow. In other embodiments the snoring detection module may be located outside pillow 40 system.

Figure 2A:
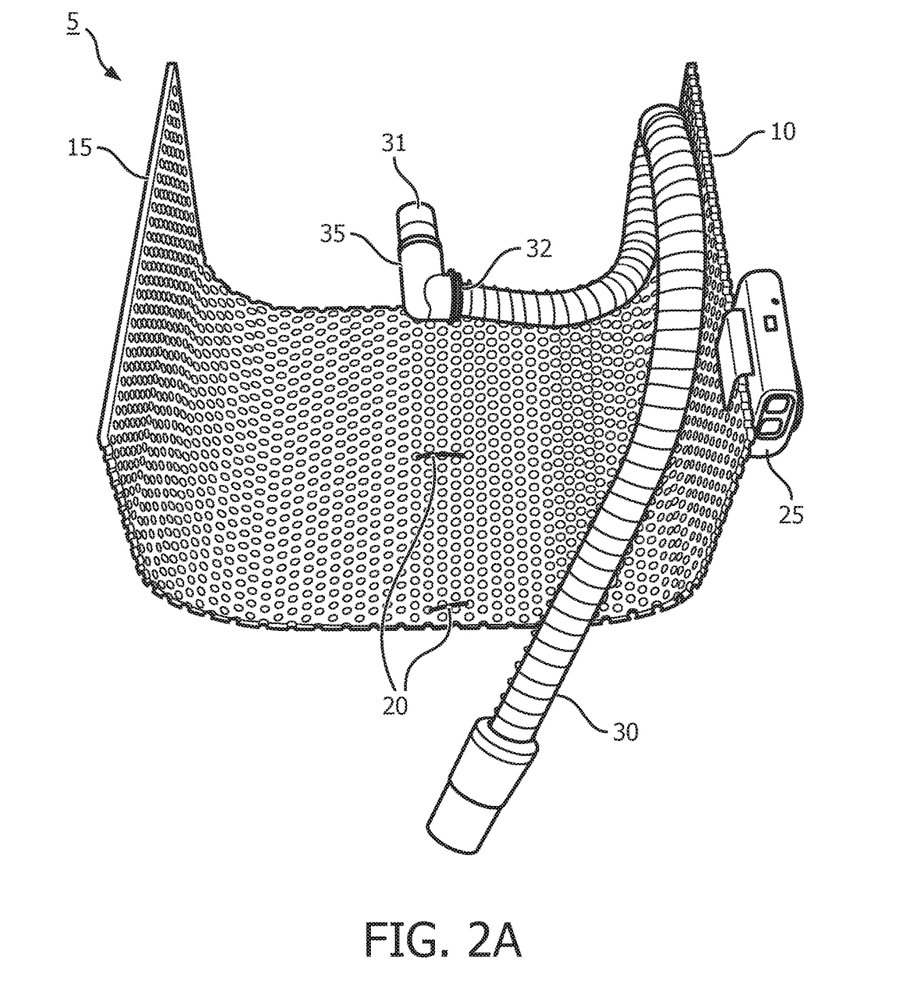
FIGS. 2A and 2B illustrate a frame used in one embodiment of the pillow system to be used with a positive airway pressure system.
Figure 6:
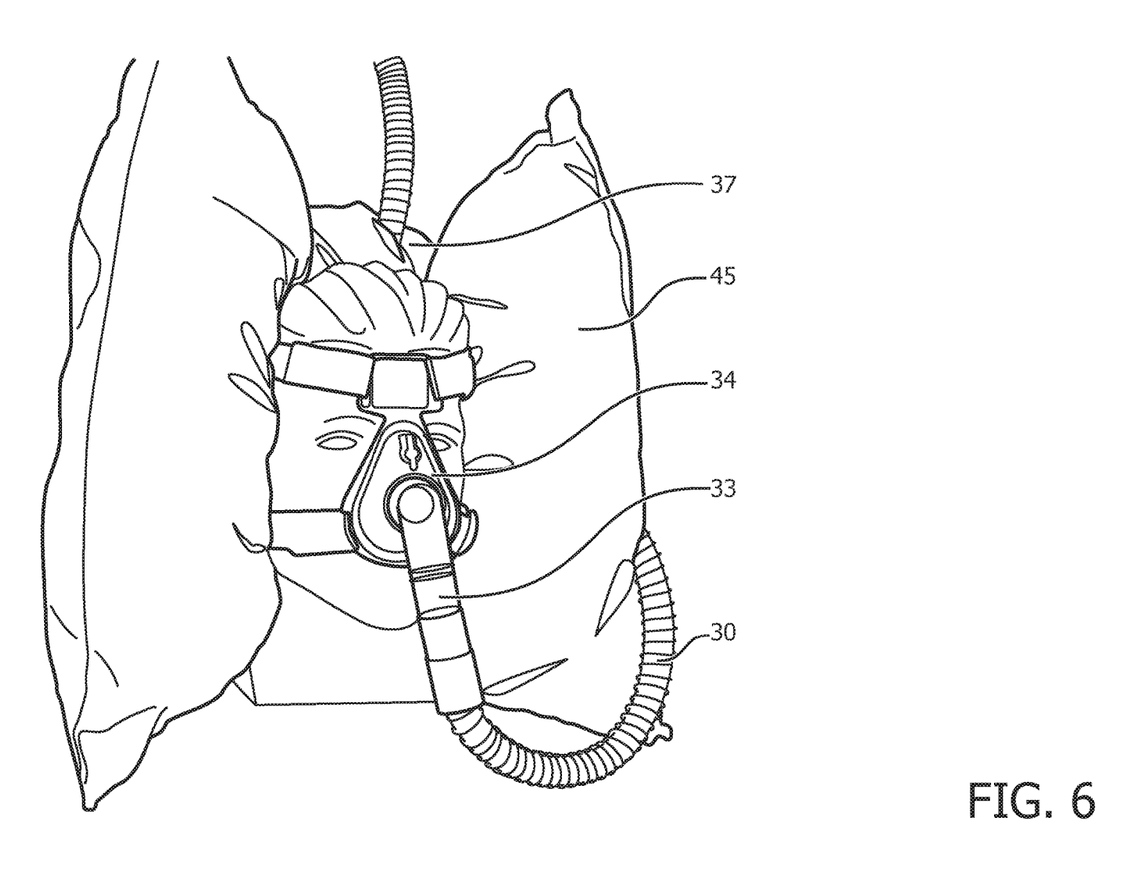
FIG. 6 depicts an exemplary embodiment of the pillow system and tubing when the subject connects his mask to a PAP system using the pillow system.

FIG. 2A illustrates a frame used in one embodiment of the pillow system to be used with a positive airway pressure system. Frame 5 in FIG. 2 is similar to that in FIG. 1 with portions 10, 15 to surround the subject's head. In FIG. 2 though, frame 5 also incorporates a tube 30 connected to a movable connection 35. The end of tube 30 that is not connected to movable connection 35 connects to a mask (e.g., mask 34 at juncture 33 as shown in FIG. 6). In some embodiments, movable connection 35 is a swivel. In other implementations movable connection 35 may provide movement of the connection about three dimensions, e.g., movable connection 35 may be or have a ball connector. In other embodiments, movable connection provides more degrees of freedom of movement, e.g., four degrees of freedom, five degrees of freedom, or six degrees of freedom. In some embodiments, (as shown in FIG. 2B) moveable connection 35 connects to a PAP system 36 and allows the subject's head to move side to side without disrupting the PAP system or any tubing 38 between the PAP system and movable connection 35.

Figure 5:
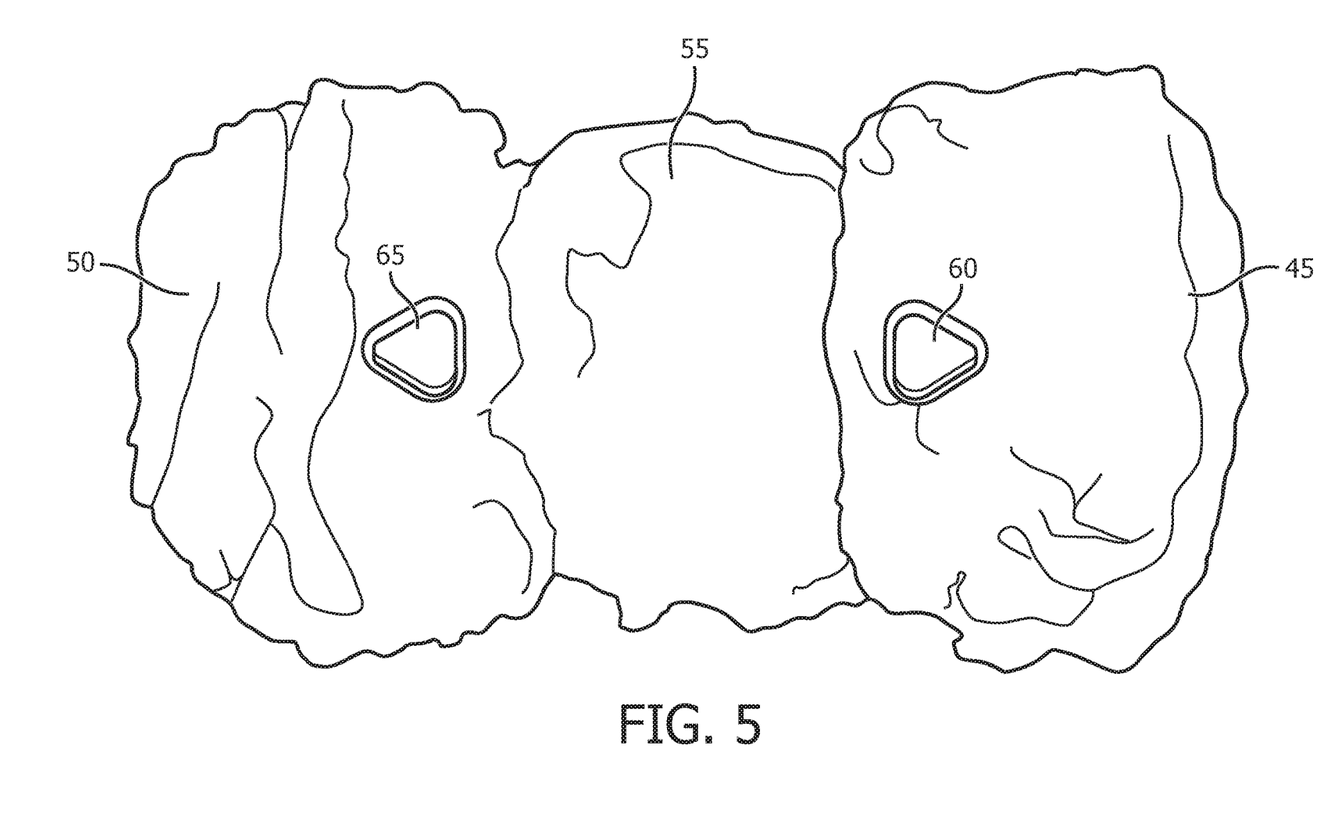
FIG. 5 illustrates an internal view of cushioning material.
Figure 7:
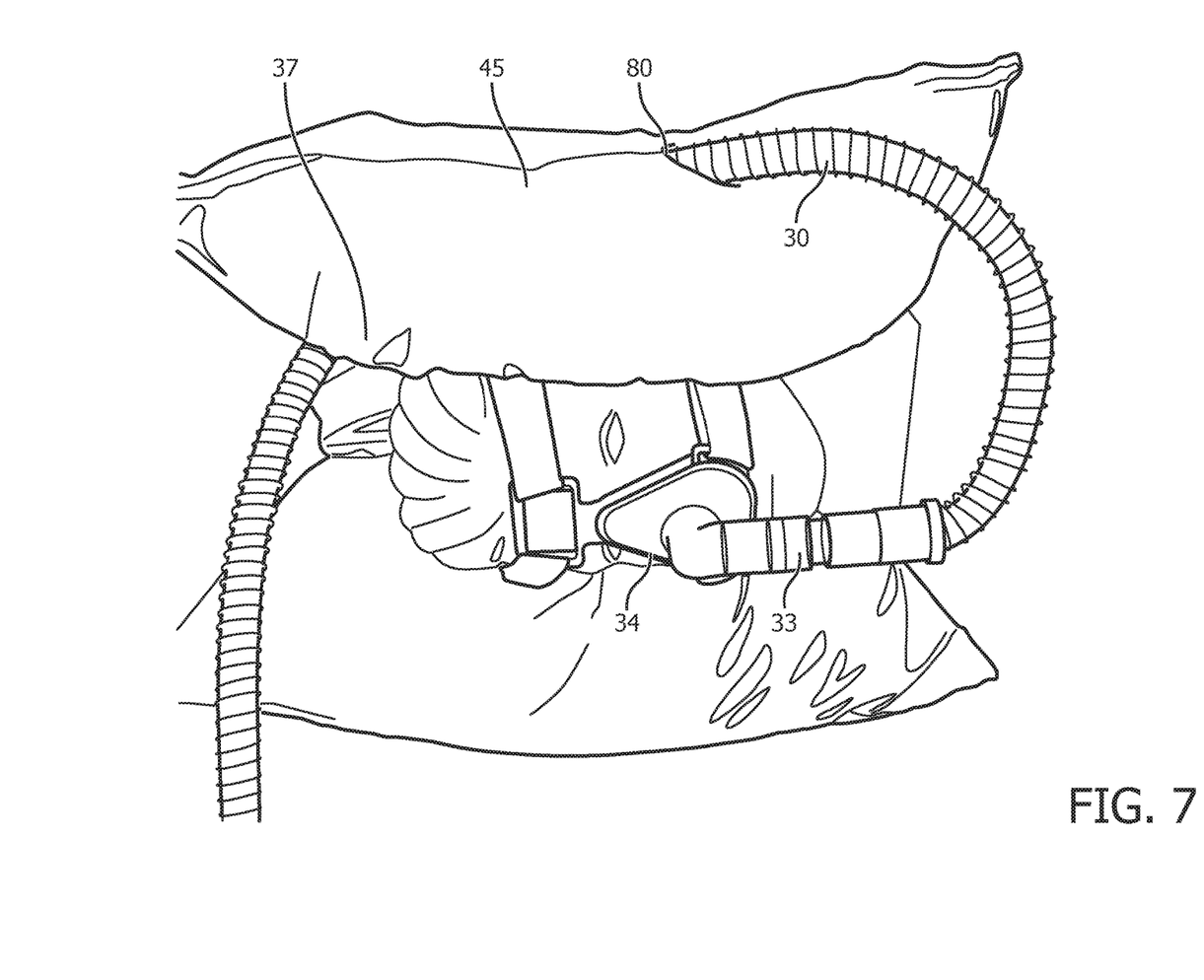
FIG. 7 depicts an exemplary embodiment of the pillow system and tubing when the subject has rolled onto his side.

Still referring to FIG. 2A, in some embodiments, moveable connection 35 may be attached to frame 5 on one side at approximately where portions 10, 15 meet. In some embodiments, movable connection 35 is located approximately in a plane with the subject's head around the crown area such that movement of the subject's head about an axis causes the moveable connection to move about the axis as well. In some embodiments, movable connection 35 has two openings 31, 32. One opening 31 provides a male or female connection to tubing 38 that is connected to a PAP system 36 (as shown in FIG. 2B). The other opening 32 provides a male or female connection to tubing 30. Tubing 30 is secured to portion 10 (or 15), typically on the inside face of the portion. Alternatively, tubing 30 may be secured to the outside face of portion 10 or 15. From connection 32, in some embodiments, tubing 30 runs along the horizontal edge of portion 10 (or 15), runs up the vertical side, and runs along the depth-wise edge of portion 10 (or 15). Although in some embodiments, tubing 30 also runs down the opposite vertical side of portion 10 (or 15), in some embodiments, tubing 30 does not. Tube 30 can be connected to the frame directly e.g., by a tie, or it can be inserted in a pass-through channel 80 between the cushioning 45, 50 and a portion 10, 15, of frame 5 (as shown in FIGS. 5, 6, 7).

In some embodiments, tube 30 is a modular hose system such as that provided by Loc-Line® (not shown). In these embodiments, the modular tube 30 runs along the same path as tubing 30 with respect to portions 10 or 15, i.e., can run inside the frame or can run outside the frame, surrounded by cushioning 45, 50 respectively in either case. If a modular tube system is used then the hose itself provides joints at regular intervals and the hose locks into place at each joint, thereby providing tension for keeping the mask 34 engaged with the subject's face, such that the mask's elastic bands can therefore be loosened or omitted altogether.

Figure 2B:
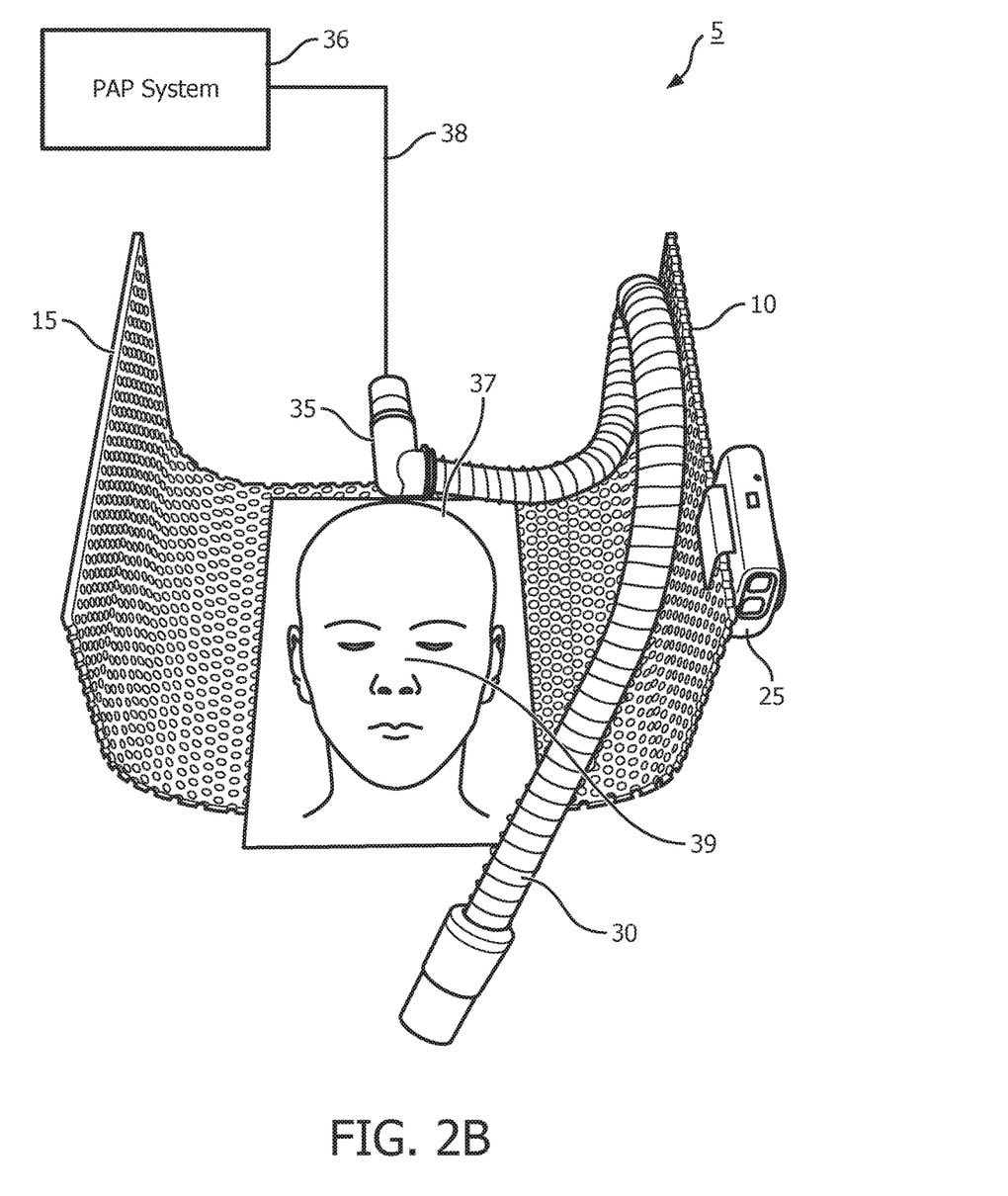

FIG. 2B illustrates frame 5 of FIG. 2A with an outline of a subject's head for reference. As shown in FIG. 2B, portion 10 is adjacent to the left side of the subject's head. Portion 15 is adjacent to the right side of the subject's head. Movable connection 35 is proximate to the crown of the subject's head and adjustable portion 20 is located proximate to the back 39 of the subject's head and connects portion 10 and portion 15. FIG. 2B also demonstrates a PAP system 36 connected to movable connection 35, typically by a tube 38 adapted for delivering breathable gas.

Figure 3:
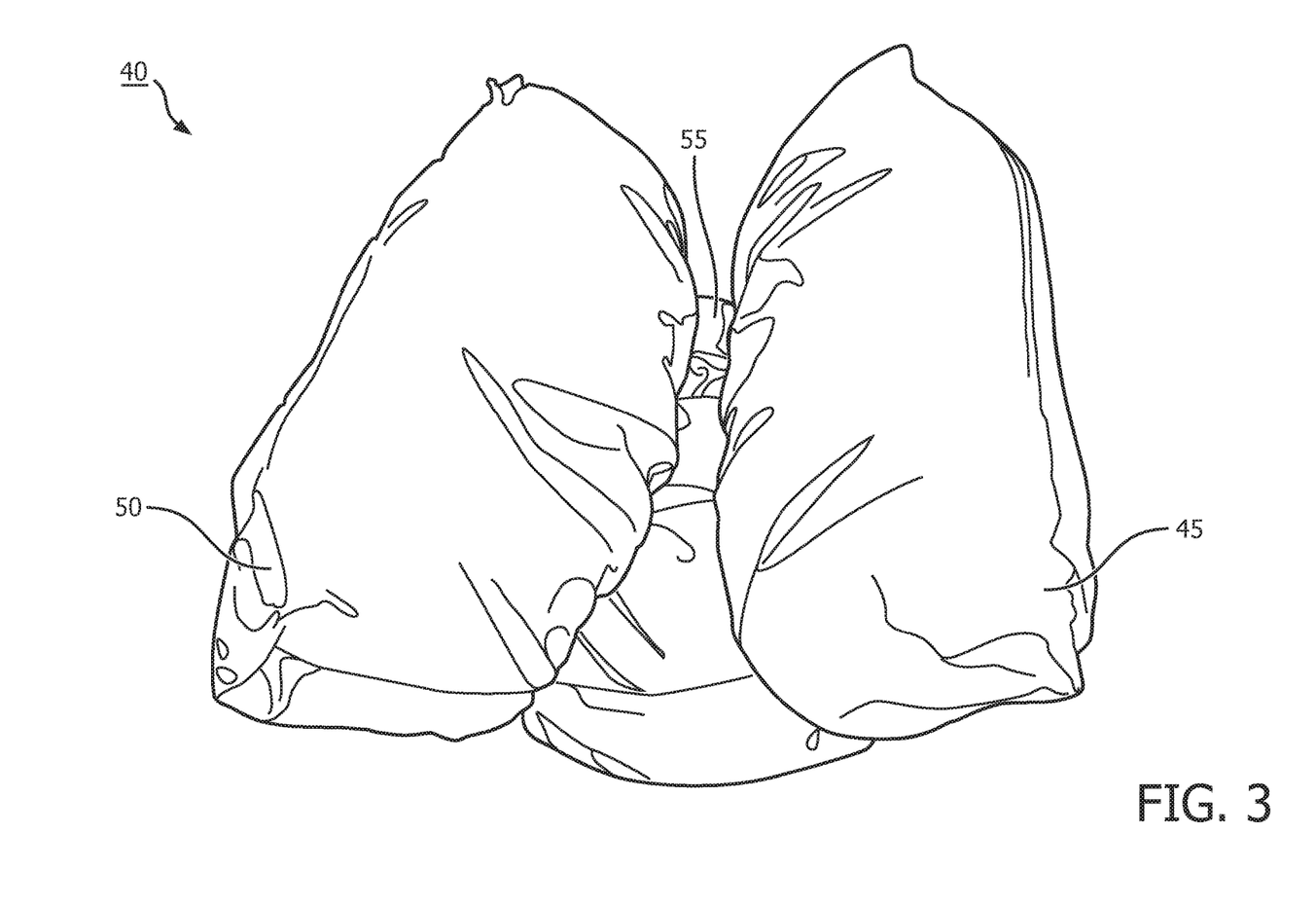
FIG. 3 depicts an exemplary view of a pillow system complete with cushioning.

FIG. 3 depicts an exemplary view of pillow system 40 complete with cushioning. Cushioning material 45 is held in place on the left side of the subject's head by frame portion 10 (hidden by cushioning material 45) responsive to the subject's head being in place on pillow system 40. Cushioning material 50 is held in place on the right side of the subject's head by frame portion 15 (hidden by cushioning material 50) responsive to the subject's head being in place on pillow system 40. Cushioning material 55 provides support for the back of the subject's head and covers where portions 10, 15 overlap and/or are joined by adjustable portion 20.

FIG. 4 depicts an exemplary view of a subject's head in place on pillow system 40.

FIG. 5 illustrates an exposed view of cushioning material 45, 50, 55. Cushioning material 45 includes an ear cup 60. Ear cup 60 is supported by portion 10 and/or cushioning material 45 adjacent to portion 10 at a position such that, responsive to the subject's head being in place on the pillow system 40, ear cup 60 surrounds the subject's ear on the left side of the subject's head. Similarly, cushioning material 50 includes an ear cup 65. Ear cup 65 is supported by portion 15 and/or cushioning material 50 adjacent to portion 15 at a position such that, responsive to the subject's head being in place on the pillow system 40, ear cup 65 surrounds the subject's ear on the right side of the subject's head. As just described, in some embodiments, ear cups 60, 65 may be supported by portions 10, 15, of frame 5 and cushioning material 45, 50 together. In some embodiments though, ear cups 60, 65 may be attached to frame 5 with the cushioning material just surrounding them. In still other embodiments, ear cups 60, 65 are not attached to frame 5, and instead are supported by just cushioning material 45, 50.

In some embodiments, ear cups 60, 65 include or are made from sound absorbing gels. The sound absorbing gels provide sound suppression to ensure that external sounds do not rouse the subject from sleeping. Alternatively or additionally, in some embodiments, ear cups 60, 65 each house a speaker (not shown). The speakers can provide active noise cancellation, e.g., anti-phase sound wave production, or can be connected to a sound producing device such as a radio or audio/music device, e.g., an MP3 player.

FIG. 6 depicts an exemplary implementation of pillow system 40 and tubing 30 when the subject connects his mask 34 to a PAP system using the pillow system. As shown in FIG. 6, tube 30 is secured to portion 10 and cushioning 45 such that, when the subject rolls onto his side (as shown in FIG. 7) tube 30 moves with the subject's head. Because tube 30 is connected to frame 5, when the subject moves his head to the right, pillow system 40 and tubing 30 maintain their orientations with respect to his head, i.e., cushioning 45 (surrounding portion 10) remains engaged to the left of the subject's head, cushioning 55 (surrounding parts of portions 10 and 15) remains engaged to the back of the subject's head and cushioning 50 (surrounding portion 15) remains engaged to the right of the subject's head. Tubing 30 remains in contact with cushioning 45 and moves with pillow system 40. As shown in FIG. 7, because tubing 30 is secured by portion 10 and cushioning 45, when the subject rolls right, tubing 30 rolls with him And because tubing 30 connects to movable connection 35 at a point 37 near the crown of the subject's head, tubing 30 does not roll in front of subject's face, nor is the PAP mask 34 pulled away from the subject by the subject's movement. Thus, even though the subject may move during the night, the PAP mask 34 and tubing 30 remain secure, ensuring a better sleep for the subject. As described above, tube 30 can be connected to frame 5 or it can be fed through a pass-through channel 80 on either side of the pillow system, between cushioning 45, 50 and frame 5.

In some embodiments the mask 34 is sold with the pillow system 40, moveable connection 35, and tube 30. In other embodiments, the pillow system is sold with moveable connection 35 and tube 30, but does not include the mask 34. In still other embodiments, pillow system 40 is sold with moveable connection 35, but not tube 30 or mask 34. In still other embodiments, pillow system 40 is sold with mask 34, tube 30, or moveable connection 35.

In some embodiments (not shown), the mask is fixed to the pillow system's frame using a solid hinge. The mask is able to rotate from an open position, allowing the subject to place his head in the pillow system, to a locked position where the mask is over the subject's face (though not necessarily engaged). In some of these embodiments, cushioning material 45, 50, 55 is air, and the pillow system is inflated by the subject via a valve or pump. When the mask is in the locked position, it remains at a generally fixed location. When the subject increases the amount of air present in the pillow system, the pillow system becomes tighter and more supportive of the subject's head. As this happens, the subject's head engages the mask and the subject can use the mask without the use of headgear.

Figure 8:
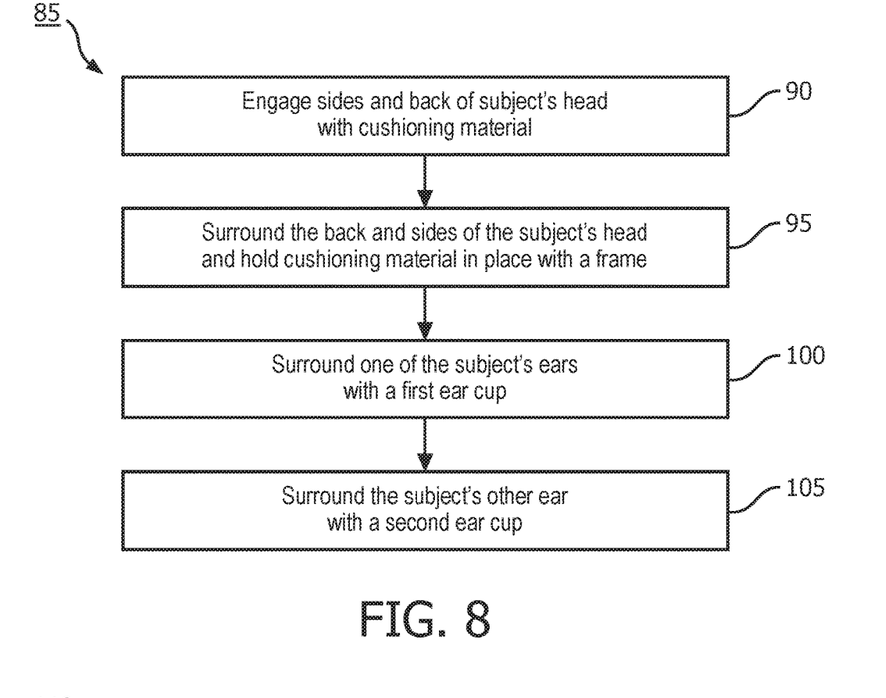
FIG. 8 depicts a method used in a pillow system that includes a cushioning material, a resilient frame, a first ear cup and a second ear cup.

FIG. 8 depicts a method 85 used in a pillow system that includes a cushioning material, a resilient frame, a first ear cup and a second ear cup. The method 85 begins by engaging the sides and back the subject's head using cushioning material responsive to the subject's being in place on the pillow system at operation 90. A resilient frame then surrounds the back and sides of the subject's head, and holds the cushioning material in place on the subject's head responsive to the subject's head being in place on the pillow system at operation 95. When the subject's head is placed on the pillow system, an ear cup surrounds one of the subject's ears and another ear cup surrounds at operation the subject's other ear at operations 100, 105. The ear cups provide sound suppression as described herein. The frame can be adjusted to accommodate differences in distances between the first side of the head and the second side of the head for different subjects. The method also includes, in some instances, providing active noise cancellation via speakers housed in each of the ear cups. Additionally or alternatively, sound can be output via speakers housed in each of the ear cups. This usually involves putting each speaker in signal communication with a sound producing device such as a radio or audio/music device, e.g., an MP3 player.

In some embodiments, there is a snoring detection system. The snoring detection system executed on one or more processors, and can detect that the subject is snoring, e.g., by receiving sound input via a microphone and determining that sounds received are above a certain volume threshold. If the subject is determined to be snoring, alarm clock 25 can be activated in response to raise the subject to a less-deep sleep stage.

Figure 9:
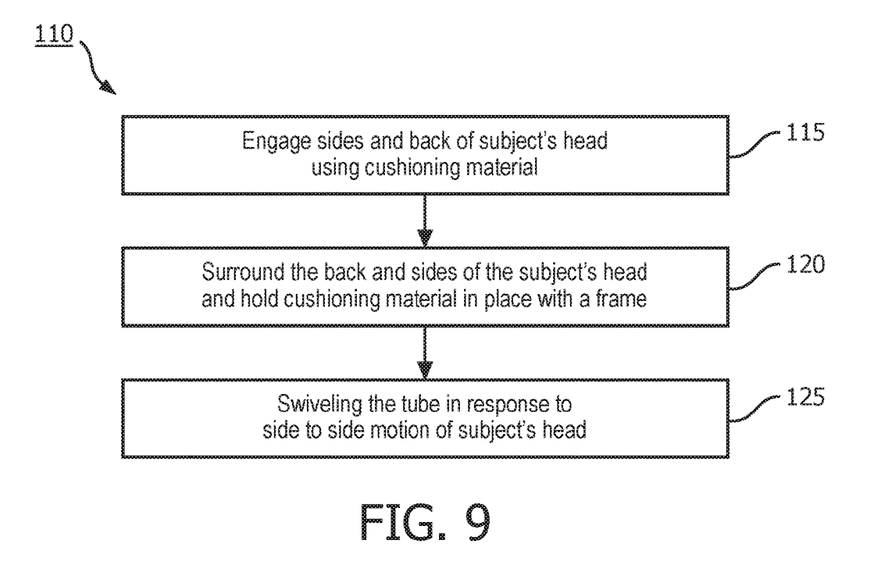
FIG. 9 depicts a method used in a pillow system that includes a cushioning material, a tube connected to a moveable connection, and a resilient frame with a first portion and a second portion.

FIG. 9 depicts a method 110 used in a pillow system that includes a cushioning material, a tube connected to a movable connection, and a resilient frame with a first portion and a second portion. The method 110 begins by engaging the sides and back the subject's head using cushioning material, responsive to the subject's being in place on the pillow system at operation 115. A resilient frame then surrounds the back and sides of the subject's head, and holds the cushioning material in place on the subject's head responsive to the subject's head being in place on the pillow system at operation 120. A tube is then moved at operation 125 in response to any movement of the subject's head.

In some embodiments, the method also includes slidably connecting the first portion and second portions of the frame via springs to bias the first portion toward the second portion. This provides adjustment to accommodate differences in distances between the first side of the head and the second side of the head for different subjects.

In some scenarios, the method also includes providing a sound absorbing gel within ear cups supported by the first and second portions of the frame and/or the cushioning material. Additionally or alternatively, the method can include providing active noise cancellation via speakers located within each of the ear cups. And, in some cases, an alarm clock housed within the cushioning material is activated, either as programmed by the subject or in response to a snore detecting module detecting that the subject is snoring.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A pillow system configured to engage a back and sides of a subject's head, the pillow system comprising:
   a cushioning material configured to engage the back and sides of the subject's head responsive to the head of the subject being in place on the pillow system,
   a substantially rigid U-shaped frame configured to surround the back and sides of the subject's head and the cushioning material, the U-shaped frame being relatively rigid in relation to the cushioning material in order to support and to hold the cushioning material in place on the subject's head for movement therewith, the substantially rigid U-shaped frame comprising:
      a first portion having a first inner side and a first outer side, the first portion being configured to hold the cushioning material in place on a first side of the subject's head responsive to the subject's head being in place on the pillow system;
      a second portion having a second inner side and a second outer side, the second portion being configured to hold the cushioning material in place on a second side of the subject's head responsive to the subject's head being in place on the pillow system;
      an adjustable portion at a location proximate to the back of the subject's head that slidably connects the first portion and the second portion, the adjustable portion providing lateral adjustment to relatively slide the first portion and the second portion to a fixed distance and being configured to retain spacing between the first portion and the second portion at the fixed distance, in order to accommodate differences in distances between the first side of the head and the second side of the head for different subjects;
      wherein at least one of the first portion, the second portion, and the adjustable portion are configured to flex relative to one another under force;
   a first ear cup supported by the first portion and/or the cushioning material adjacent the first portion at a position such that, responsive to the subject's head being in place on the pillow, the first ear cup surrounds the subject's ear on a first side of the subject's head; and
   a second ear cup supported by the second portion and/or the cushioning material adjacent the second portion at a position such that, responsive to the subject's head being in place on the pillow, the second ear cup surrounds the subject's ear on a second side of the subject's head,
   wherein, via the substantially rigid U-shaped frame and its adjustable portion, the cushioning material maintains its engagement with respect, to both the first side and the second side of the subject's head during movement of the subject's head to different positions.

2. The pillow system of claim 1, wherein the adjustable portion comprises one or more of a set of one or more springs that slidably connect the first portion and second portion and biases the first portion toward the second portion; a ball catch system, wherein perforation holes in the first portion and the second portion are the catch of the ball catch system; and/or a bendable material that resiliently maintains shape if adjusted.

3. The pillow system of claim 1 further comprising an alarm clock.

4. The pillow system of claim 3 further comprising a microphone and one or more processors configured to execute a snoring detection module that detects whether or not the subject is snoring based on signals generated by the microphone.

5. The pillow system of claim 1 wherein the first and second ear cups each comprise a noise-cancelling gel.

6. The pillow system of claim 1 further comprising a speaker housed in each of the first and second ear cups, each speaker providing active noise cancellation.

7. A method, used in a pillow system that includes a cushioning material, a substantially rigid U-shaped frame with a first portion and a second portion connected by an adjustable portion, a first ear cup and a second ear cup, the method comprising:
   engaging, by the cushioning material, a back and sides of a subject's head responsive to the head of the subject being in place on the pillow system;
   surrounding, by the substantially rigid U-shaped frame, the back and sides of the subject's head and the cushioning material, the U-shaped frame being relatively rigid in relation to the cushioning material in order to support and to hold the cushioning material in place on the subject's head for movement therewith responsive to the subject's head being in place on the pillow system and wherein at least one of the first portion, the second portion, and the adjustable portion are configured to flex relative to one another under force;
   facilitating lateral adjustment, by the adjustable portion, of a slidable connection between the first portion and the second portion by sliding the first portion and the second portion to a fixed distance and retaining a relative spacing between the first portion and the second portion at the fixed distance, wherein the adjustment accommodates differences in distances between the first side of the head and the second side of the head for different subjects;
   surrounding, by the first ear cup, the subject's ear on a first side of the subject's head responsive to the subject's head being in place on the pillow system; and
   surrounding, by the second ear cup, the subject's ear on a second side of the subject's head responsive to the subject's head being in place on the pillow system,
   wherein, via the substantially rigid U-shaped frame and its adjustable portion, the cushioning material maintains its engagement with respect to both the first side and the second side of the subject's head during movement of the subject's head to different positions.

8. The method of claim 7, wherein the adjustable portion comprises one or more of a set of one or more springs, wherein the first portion and second portion are pushed apart by the sides of the subject's head; a ball catch system, wherein perforation holes in the first portion and the second portion are the catch of the ball catch system; and/or a bendable material that resiliently maintains shape if adjusted.

9. The method of claim 7 further comprising providing active noise cancellation via speakers housed in each of the first and second ear cups.

10. The method of claim 7 further comprising outputting sound via speakers housed in each of the first and second ear cups, each speaker in signal communication with a sound producing device.

11. The method of claim 7 further comprising detecting, by a snoring detection system, that the subject is snoring and in response, activating an alarm clock.

12. A pillow system, the pillow system comprising:
cushioning means for engaging a back and sides of a subject's head responsive to the head of the subject being in place on the pillow system;
a substantially rigid U-shaped surrounding means for surrounding the back and sides of the subject's head and the cushioning means, the U-shaped surrounding means being relatively rigid in relation to the cushioning material for supporting and for holding the cushioning means in place on the subject's head for movement therewith responsive to the head of the subject being in place on the pillow system and wherein at least part of the U-shaped surrounding means is configured to flex under force;
first ear surrounding means for surrounding the subject's ear on a first side of the subject's head responsive to the subject's head being in place on the pillow system; and
second ear surrounding means for surrounding the subject's ear on a second side of the subject's head responsive to the subject's head being in place on the pillow system,
wherein substantially rigid U-shaped surrounding means comprises an adjustable connecting means for slidably connecting parts of the U-shaped surrounding means to provide relative sliding movement to said parts in a lateral direction to a fixed distance and to retain spacing said parts at the fixed distance, and
wherein, via the substantially rigid U-shaped surrounding means and its adjustable means, the cushioning material maintains its engagement with respect to both the back and the sides of the subject's head during movement of the subject's head to different positions.

13. The pillow system of claim 12 wherein the substantially rigid U-shaped surrounding means further comprises:
first holding means for holding the cushioning means in place on a first side of the subject's head responsive to the subject's head being in place on the pillow system; and
second holding means for holding the cushioning means in place on a second side of the subject's head responsive to the subject's head being in place on the pillow system;
wherein the adjustable connecting means adjustably connects the first holding means and the second holding means to relatively move at least in the lateral direction and retain spacing between the first holding means and the second holding means at the fixed distance, wherein differences in distances between the first side of the head and the second side of the head for different subjects are accommodated,
wherein at least one of the first holding means, the second holding means, and the adjustable connecting means are configured to flex under force.

14. The pillow system of claim 12 fiwther comprising active noise cancellation means housed in each of the first and second holding means.

15. The pillow system of claim 12 further comprising sound output means housed in each of the first and second holding means.

16. The pillow system of claim 12 further comprising detecting means for detecting that the subject is snoring, and in response, activating an alarm means.

17. The pillow system of claim 13 wherein the adjustable connecting means comprises one or more of a set of one or more springs, wherein the first holding means and second holding means are pushed apart by the sides of the subject's head; a ball catch system, wherein perforation holes in the first portion and the second portion are the catch of the ball catch system; and/or a bendable material that resiliently maintains shape if adjusted.

* * * * *